(12) United States Patent
Maki et al.

(10) Patent No.: US 7,378,107 B2
(45) Date of Patent: May 27, 2008

(54) SERUM REMNANT-LIKE LIPOPROTEIN CONCENTRATION REGULATOR

(75) Inventors: Hideaki Maki, Yokosuka (JP); Michio Kasai, Yokosuka (JP); Yoshie Suzuki, Yokosuka (JP); Naohisa Nosaka, Yokosuka (JP); Mitsuko Okazaki, Sakado (JP); Osamu Igarashi, Hitachi (JP); Kazuo Kondo, Bunkyo-ku (JP)

(73) Assignee: The Nisshin OilliO Group, Ltd., Chuo-ku, Tokyo (JP)

( * ) Notice: Subject to any disclaimer, the term of this patent is extended or adjusted under 35 U.S.C. 154(b) by 0 days.

(21) Appl. No.: 11/222,741

(22) Filed: Sep. 12, 2005

(65) Prior Publication Data

US 2006/0034896 A1 Feb. 16, 2006

Related U.S. Application Data

(63) Continuation of application No. PCT/JP2004/03000, filed on Mar. 9, 2004.

(30) Foreign Application Priority Data

Mar. 13, 2003 (JP) .............................. 2003-068665

(51) Int. Cl.
*A61K 47/00* (2006.01)
*A61K 31/56* (2006.01)
*A61K 31/355* (2006.01)
*A61K 31/225* (2006.01)
*A01N 45/00* (2006.01)
*A01N 37/02* (2006.01)

(52) U.S. Cl. ...................... 424/439; 424/776; 514/171; 514/458; 514/547

(58) Field of Classification Search ................ 424/439, 424/776; 514/171, 458, 547
See application file for complete search history.

(56) References Cited

U.S. PATENT DOCUMENTS

| 3,450,819 A | * | 6/1969 | Barsky et al. | ............... 514/557 |
| 2004/0071751 A1 | * | 4/2004 | Maki et al. | .................. 424/439 |
| 2004/0142018 A1 | * | 7/2004 | Takeuchi et al. | ............ 424/439 |

FOREIGN PATENT DOCUMENTS

| EP | 0 537 113 A1 | 4/1993 |
| JP | 57-047446 | 3/1982 |
| JP | 2-207764 | 8/1990 |
| JP | 6-007113 | 1/1994 |

OTHER PUBLICATIONS

Nutrition Facts and Analysis for Oil (primary safflower oil) Jun. 19, 2006 p. 4 of 4.*
Derwent-Acc-No. 1982-33891E abstacting Kajimoto et al. JP57047446A 1982 2 pages.*
The Japanese Society of Nutrition and Food Science, Dai 56 Kai The Japanese Society of Nutrition and Food Science Taikai, Koen Yoshishu, Jun. 20, 2002, p. 319 (cited in International Search Report).
Robert W. Mahley, "Atherogenic Lipoprotein and Coronary Artery Disease: Concepts Derived from Recent Advances in Cellular and Molecular Biology", Circulation, An Official Journal of the American Heart Association, Inc., Nov. 1985, pp. 943-948, vol. 72, No. 5 (cited in the specification).
Shotaro Kosaka, et al., "Evidence of Macrophage Foam Cell Formation by Very Low-Density Lipoprotein Receptor", Circulation, Feb. 27, 2001, pp. 1142-1147 (cited in the specification).
Donald B. Zilversmit, "Atherogenesis: A Postprandial Phenomenon", Circulation, George Lyman Duff Memorial Lecture, Sep. 1979, pp. 473-485, vol. 60, No. 3 (cited in the specification).
Fredrik Karpe et al., "Postprandial Lipoproteins and Progression of Coronary Atherosclerosis", Atherosclerosis, 1994, pp. 83-97, vol. 106, Elsevier Science Ireland Ltd. (cited in the specification).
Katsuyuki Nakajima et al., "Cholesterol in Remnant-Like Lipoproteins in Human Serum Using Monoclonal Anti APO B-100 and Anti APO A-1 Immunoaffinity Mixed Gels", Clinica Chimica Acta, 1993, pp. 53-71, vol. 223, Elsevier Science Publishers B.V. (cited in the specification).
Carlo Calabrese et al., "A Cross-Over Study of the Effect of Single Oral Feeding of Medium Chain Triglyceride Oil vs. Canola Oil on Post-Ingestion Plasma Triglyceride Levels in Healthy Men", Alternative Medicine Review, 1999, pp. 23-28, vol. 4, No. 1 (cited in the specification).
Form PCT/ISA/210 (International Search Report dated Jun. 15, 2004).
Form PCT/ISA/237 (Written Opinion of the International Searching Authority dated May 31, 2004).

* cited by examiner

*Primary Examiner*—Johann Richter
*Assistant Examiner*—Ernst V Arnold
(74) *Attorney, Agent, or Firm*—Buchanan Ingersoll & Rooney PC (57) ABSTRACT

The present invention discloses serum remnant-like lipoprotein concentration regulators containing triglyceride of medium-chain fatty acids, wherein 90% or more by weight of the fatty acids as components of the medium-chain triglyceride are saturated fatty acids having 8 and 10 carbon atoms; weight ratio between the saturated fatty acids having 8 carbon atoms and those having 10 carbon atoms is 60/40 to 85/15; and the proportion of the saturated fatty acids having 8 carbon atoms in all the fatty acids bonding to the second position of the triglyceride is 60 to 85 % by weight. The present invention also discloses foods for controlling the concentration of serum remnant-like lipoproteins and pharmaceutical compositions for controlling the concentration of serum remnant-like lipoproteins, which contain the serum remnant-like lipoprotein concentration regulator. The foods for controlling the concentration of serum remnant-like lipoproteins can be easily used without concerning about side effects and restrictive diet.

9 Claims, 4 Drawing Sheets

SERUM REMNANT-LIKE LIPOPROTEIN CONCENTRATION REGULATOR

BACKGROUND OF THE INVENTION

The present invention relates to compositions which intend to control the concentration of serum remnant-like lipoproteins. In detail, the present invention relates to serum remnant-like lipoprotein concentration regulators which can control increase oft he concentration of human serum remnant-like lipoproteins in safety and to the appropriate range; foods for controlling the concentration of serum remnant-like lipoproteins which contain the serum remnant-like lipoprotein concentration regulators; and pharmaceutical compositions for controlling the concentration of serum remnant-like lipoproteins.

Serum remnant-like lipoproteins are usually transitory intermediate metabolites which are produced by hydrolysis of lipoproteins such as chylomicron lipoproteins (CM) of intestinal origin and very low density lipoproteins (VLDL) of hepatic origin, which are rich in neutral fat, by lipoprotein lipase. The former is referred to as CM remnants and the latter is referred to as VLDL remnants. Both remnant-like lipoproteins are relatively rich in cholesterol. Though those serum remnant-like lipoproteins are usually metabolized immediately and exist little in bodies of healthy people which are hungry in the early morning, they persist in the blood and increase when metabolizing process thereof is impaired. As a typical case of so-called hyper remnant lipoproteinemia which is induced by persistence of remnant-like lipoproteins in the blood, type III familial hyperlipidemia is known, wherein metabolism of serum remnant-like lipoproteins is impaired and the serum remnant-like lipoproteins become in stasis and accumulate. In addition, since serum remnant-like lipoproteins have relatively high cholesterol content among triglyceride-rich lipoproteins, they are easily ingested into vessel walls. As a result, cholesterol in serum remnant-like lipoproteins is easily accumulated in vessel walls. Further, as serum remnant-like lipoproteins are ingested into a macrophage and convert the macrophage into foam cells which are incipient lesion of arterial sclerosis (Mahley R. W., "Atherogenic lipoproteins and coronary artery disease: concepts derived from recent advances in cellular and molecular biology", Circulation (U.S.A.), vol. 72, No. 5, 943-948, 1985, and Kosaka S. et al., "Evidence of macrophage foam cell formation by very low-density lipoprotein receptor", Circulation (U.S.A.), vol. 103, No. 8, 1142-1147, 2001), serum remnant-like lipoproteins which increase in the blood though eating are paid attention to as a risk factor of onset of arterial sclerosis. Since human have many opportunities to eat between meals besides three meals a day, it is thought that they are in a postprandial state rather than on an empty stomach a lot of time of the day. Thus, importance of research on postprandial hyperlipidemia (that is, hyperlipidemia which shows abnormal amplification of serum lipids after eating though one is in normolipemic status when he/she is hungry in the early morning, or shows persistence of amplification thereof) has been emphasized for recent years, while previously questioned was a level of serum lipids which was calculated based on the blood collected on an empty stomach. In postprandial hyperlipidemia, CM and CM remnants constitute major part of serum lipids, and CM remnants' evoking of arterial sclerosis has been pointed out for a while (Zilversmit D. B., "Atherogenesis: a post-prandial phenomenon", Circulation (U.S.A.), vol. 60, No. 3, 473-485, 1979, and Karpe F et al., "Postprandial lipoproteins and progression of coronary atherosclerosis", Atherosclerosis (Netherlands), vol. 106, No. 1, 83-97, 1994). Therefore, it is very important in terms of preventing onset of arterial sclerosis and treatment after onset thereof that serum remnant-like lipoproteins are made reduced. Since improvement of daily diet occupies an important place in preventing onset of arterial sclerosis, there are desired those which can be easily ingested in everyday life, lower postprandial serum remnant-like lipoproteins and be used without concerning about side effects.

Conventionally, quantity of serum remnant-like lipoproteins is determined by immunosorbent assay. Immunosorbent assay is a commonly used method as analysis method of serum remnant-like lipoprotein and is carried out by determination of cholesterol contained in serum remnant-like lipoprotein (hereinafter referred to as serum RLP-cholesterol) as a value reflecting serum remnant-like lipoproteins. For details, it is the analysis method comprising steps of adding samples to suspension of a buffer and an insoluble support to which anti-human apo A-I and apo B-100 monoclonal antibodies are immobilized, slowly mixing by shaking and standing still; adding a enzyme reagent(s) which reacts to cholesterol part in serum remnant-like lipoproteins to a supernatant fluid containing serum remnant-like lipoproteins which did not react with the antibodies; and determining the amount of cholesterol in the supernatant fluid (Nakajima K. et al., "Cholesterol in remnant-like lipoproteins in human serum using monoclonal anti apo B-100 and anti apo A-I immunoaffinity mixed gels", Clin Chim Acta (Netherlands), vol. 223, Nos. 1 and 2, 53-71, 1993). Among apo proteins existing in serum, CM and high density lipoproteins (HDL) have apo A-I, and VLDL and low density lipoproteins (LDL) have apo B-100. They bond with each of antibodies to precipitate, and remnant-like lipoproteins (CM remnants and VLDL remnants) exist as nonbonding fractions in supernatant fluid thereof. The cholesterol value in these fractions is regarded as that reflecting remnant-like lipoproteins and determined clinically in our country.

Medium-chain triglyceride (triglyceride of medium-chain fatty acids) has been used as solvents for oil-soluble flavoring/coloring agents for food; mold release/lubricating oils for food; or pharmaceutical raw materials because it has high oxidation stability, low freezing point and viscosity, high solubility and it is also transparent and colorless. Further, as medium-chain triglyceride has high absorbability and energy proportion thereof are higher than that of sugar groups, it has also been used as raw materials of enteral nutrients, wherein efficient energy supplementation is intended.

It has also been reported that controlling effect of postprandial neutral fat concentration in the blood (inhibiting effect on elevation thereof) is brought by replacing dietary fat and oil with medium-chain triglyceride (Calabrese, C. et al., "A cross-over study of the effects of a single oral feeding of medium chain triglyceride oil vs. canola oil on post-ingestion plasma triglyceride levels in healthy men", Alternative Medicine Review (U.S.A.), vol. 4, No. 1, 23-28, 1999). However, it has not yet been discovered that medium-chain triglyceride has inhibiting function on elevation of the concentration of serum remnant-like lipoproteins.

DISCLOSURE OF THE INVENTION

An object of the present invention is to provide serum remnant-like lipoprotein concentration regulators which can be easily used without concerning about side effects and restrictive diet.

Another object of the present invention is to provide foods for controlling the concentration of serum remnant-like lipoproteins which contain the serum remnant-like lipoprotein concentration regulators; and pharmaceutical compositions for controlling the concentration of serum remnant-like lipoproteins.

The inventors have studied the above problems to be solved and found that triglyceride of medium-chain fatty acids has an excellent effect for controlling the concentration of serum remnant-like lipoproteins and can be easily ingested in daily life and, therefore, it is useful as foods, pharmaceutical compositions and the like. The present invention has been completed on the basis of this finding.

Namely, the present invention provides serum remnant-like lipoprotein concentration regulators containing triglyceride of medium-chain fatty acids.

The present invention also provides serum remnant-like lipoprotein concentration regulators containing triglyceride of medium-chain fatty acids, wherein 90% or more by weight of the fatty acids as components of the triglyceride of medium-chain fatty acids are saturated fatty acids having 8 and 10 carbon atoms; weight ratio between the saturated fatty acids having 8 carbon atoms and those having 10 carbon atoms is 60/40 to 85/15; and the proportion of the saturated fatty acids having 8 carbon atoms in all the fatty acids bonding to the second position of the triglyceride is 60 to 85% by weight.

Further, the present invention provides serum remnant-like lipoprotein concentration regulators which contain 40% or more by weight of triglyceride of medium-chain fatty acids.

In addition, the present invention provides use of the serum remnant-like lipoprotein concentration regulators for controlling the concentration of serum remnant-like lipoproteins of human whose BMI level is 23 or higher.

Similarly, the present invention also provides a method(s) for controlling the concentration of human serum remnant-like lipoproteins, comprising the step of administering, preferably orally, the serum remnant-like lipoprotein concentration regulator to human, especially those whose BMI level is 23 or higher.

Further, the present invention provides foods for controlling the concentration of serum remnant-like lipoproteins which contain the serum remnant-like lipoprotein concentration regulator.

The present invention also provides pharmaceutical compositions for controlling the concentration of serum remnant-like lipoproteins which contain the serum remnant-like lipoprotein concentration regulator.

BEST MODE FOR CARRYING OUT THE INVENTION

Triglyceride of medium-chain fatty acids in the present invention is triglyceride wherein medium-chain fatty acids are constituent fatty acids, namely, triacylglycerol. Medium-chain fatty acids in the present invention are fatty acids having 6 to 12 carbon atoms, particularly preferably saturated fatty acids, and further preferably saturated fatty acids having even-numbered carbon atoms. For example, it includes caproic acid, caprylic acid, capric acid and lauric acid. Preferred ones are caprylic acid and capric acid both of which are saturated fatty acids having 8 to 10 carbon atoms. Further, it is also preferable that 90% or more by weight (more preferably 95 to 100% by weight) of the fatty acids as components of the triglyceride of medium-chain fatty acids are saturated fatty acids having 8 and 10 carbon atoms; weight ratio between the saturated fatty acids having 8 carbon atoms and those having 10 carbon atoms is 60/40 to 85/15 (more preferably 7:3 to 8:2); and the proportion of the saturated fatty acids having 8 carbon atoms in the composition of fatty acids bonding to the second position of the triglyceride is 60 to 85% by weight (more preferably 65 to 80% by weight).

The production methods of this triglyceride of medium-chain fatty acids are not particularly limited. For example, triglyceride of medium-chain fatty acids can be obtained by ester bond reaction using medium-chain fatty acids derived from palm kernel oil or cocoanut oil and glycerin as raw materials. The conditions of the ester bond reaction are not particularly limited and, for example, it can be obtained by the reaction under pressure without any catalysts and any solvents. Of course, the triglyceride of medium-chain fatty acids can be obtained by the reaction using a catalyst(s) or a solvent(s). By mixing triglyceride of medium-chain fatty acids and medium-chain fatty acids wherein blend ratio is devised, and using lipase having a positional specificity such as "Lipase PL" produced by Meito Sangyo Co., Ltd., it is possible to obtain triglyceride of medium-chain fatty acids wherein 90% or more by weight of the fatty acids as components of the triglyceride are saturated fatty acids having 8 and 10 carbon atoms; weight ratio between the saturated fatty acids having 8 carbon atoms and those having 10 carbon atoms is 60/40 to 85/15; and the proportion of the saturated fatty acids having 8 carbon atoms to the composition of fatty acids bonding to the second position of the triglyceride is 60 to 85% by weight. It is also possible to obtain triglyceride of medium-chain fatty acids itself from oil seeds of gene recombinant plants, or to produce triglyceride of medium-chain fatty acids using medium-chain fatty acids as raw materials, which are obtained from oil seeds of gene-recombinant plants.

In the present invention, serum remnant-like lipoproteins are transitory intermediate metabolites which are produced by hydrolysis of lipoproteins such as CM of intestinal origin and VLDL of hepatic origin, which are rich in neutral fat, by lipoprotein lipase. The former is referred to as CM remnants and the latter is referred to as VLDL remnants. Both remnant-like lipoproteins are relatively rich in cholesterol and easily accumulated in vessel walls and, therefore, their activity evoking arterial sclerosis has been concerned. Among them, lipoproteins are a complex of lipids and proteins and mainly consist of the four kinds, that is, CM, VLDL, LDL and HDL. Neutral fat is triglyceride contained in the blood. Serum is supernatant which is obtained, in order to analyze lipids in the blood, by leaving the collected blood in a test tube(s); and a component wherein blood cells and blood platelets are removed.

In the present invention, control of the concentration of serum remnant-like lipoproteins indicates the controlling function of the concentration of the serum remnant-like lipoproteins such as inhibiting the increase of the concentration of the serum remnant-like lipoproteins after eating in case that the increase of the postprandial concentration is caused by ingesting lipids such as ordinary cooking oils (for example, blend oils) through diet; and having no effect to the concentration in case that the concentration of the serum remnant-like lipoproteins is appropriate. Here, "after eating (or postprandial)" in the present invention indicates the status after ingesting lipids such as animal and plant fats and oils.

Serum remnant-like lipoprotein concentration regulators of the present invention preferably contain 5% or more by weight of the triglyceride of medium-chain fatty acids, particularly preferably 5 to 100% by weight thereof and further more preferably 40 to 99.95% by weight thereof. They also preferably contain 95 to 100% by weight of the triglyceride of medium-chain fatty acids.

The present invention also provides serum- remnant-like lipoprotein concentration regulators which contain 40% or more by weight of common triglycerides of medium-chain fatty acids. The serum remnant-like lipoprotein concentration regulators preferably contain 40 to 99.95% by weight of the triglyceride of medium-chain fatty acids and particularly preferably 48 to 99.95% by weight thereof. They also preferably contain 95 to 100% by weight of the triglyceride of medium-chain fatty acids.

The serum remnant-like lipoprotein concentration regulators of the present invention can contain components other than triglyceride of medium-chain fatty acids. The components are not particularly limited, and examples thereof include ordinary cooking fats and oils such as soybean oil, canola oil, high oleic acid canola oil, corn oil, sesame seed oil, sesame salad oil, perilla oil, flax seed oil, peanut oil, safflower oil, high oleic acid safflower oil, sunflower oil, high oleic acid sunflower oil, cotton seed oil, grape seed oil, macadamia nut oil, hazelnut oil, pumpkin seed oil, walnut oil, camellia oil, tea seed oil, egoma seed oil, borage oil, olive oil, rice oil, rice-bran oil, wheat germ oil, palm oil, palm kernel oil, cocoanut oil, cacao butter, beef tallow, lard, chicken fat, dairy cream, fish oil, seal oil, algae oil, and fats and oils thereof which are low-saturated by breed improvement, and hydrogenated fats and oils and separated fats and oils thereof. Further, including vitamin E and plant sterol, it is also possible to add ester of polyglycerin fatty acid, ester of sucrose fatty acid, ester of sorbitan fatty acid, ester of ascorbic acid-dependent lipid peroxidation, monoglyceride of organic acid, lignan, coenzyme Q, amino acid, methyl sulfonylmethane, glucosamine, chondroitin, ascorbyl stearate, ascorbyl palmitate, phospholipid, oryzanol, diglyceride and the like thereto.

Meanwhile, the vitamin E is a genetic term of various tocopherols and tocotrienols which are highly contained in plants and grains, and each are classified into four kinds, that is, $\alpha$, $\beta$, $\gamma$, $\delta$. They may also be synthetic products.

The plant sterol is also referred to as phytosterol, and includes, for example, sitosterol, sitostanol, stigmasterol, stigmastanol, campesterol, campestanol, fucosterol, isofucosterol, clerosterol, 2,2-dihydroclerosterol, spinasterol, 2,2-dihydrospinasterol, avenasterol, 2,2 $\beta$-ethyl-2,5-dehydrolathosterol, 2,5-dehydrochondrillasterol and brassicasterol. They are sterol compounds of plant origin and those which are widely distributed in oil seeds and grains. They may also be synthetic products.

Among these, it is preferable to contain one kind or more selected from a group consisting of animal and plant fats and oils, vitamin E, and plant sterol. When an animal and plant fat(s) and oil(s) is contained, it is preferably 60% or less by weight to all, more preferably 5 to 55% by weight thereof and particularly preferably 5 to 50% by weight. When vitamin E is contained, it is preferably 0.01 to 5% by weight to all and more preferably 0.01 to 2% by weight. When plant sterol is contained, it is preferably 0.5 to 6% by weight to all and more preferably 1 to 4% by weight.

As the animal and plant fats and oils, for instance, it is also possible to use cooking fats and oils which are obtained by dealing cooling fats and oils with ester exchange, wherein two kinds or more of the cooking fats and oils are mixed. The ester exchange includes a chemical reaction using an alkali catalyst(s) and an enzymatic reaction using an enzyme(s). The enzymatic reaction is preferable in terms of flavor and color of the cooking fats and oils, but not particularly limited to this. Further, bias may or may not exist between compositions in fatty acids located in the first and third positions of the obtained cooking fats and oils by ester exchange, and a fatty acid(s) located in the second position thereof.

Body-mass index: BMI used in the present invention is a numerical value pharmaceutically used in determination of obesity, and calculated by body weight (kg)/body height (m)/body height (m) and its unit is $kg/m^2$. Since BMI level is easily calculated by using measured values of the body weight and height, it is generally used as an alternative to methods for measuring body fat which need time and an equipment(s) for measurement, such as methods for measuring the body density typified by underwater weighing method and air displacement method; measurement of total body potassium; and bioimpedance method. It has been discovered from the prior studies that the neutral fat and cholesterol values in the blood of those who are hungry in the early morning increase with the increase of their BMI levels [Seiichiro Tarui, et al., "Seijin-Himan/Shoni-Himan no Seiin to Byotai nikansuru Sogotekikenkyu" (Comprehensive Studies regarding causes of occurrence and pathologies in adult/childhood obesity), Kose-sho fiscal Showa 59 Kaken Sogo Kenkyu Seika Hokokusho (Reports of Comprehensive Study Results of scientific research of Ministry of Health, Labour and Welfare in fiscal Showa 59), 1985]. In case that the increase of the concentration of serum remnant-like lipoproteins is caused by ingesting lipids through diet, use of the serum remnant-like lipoprotein concentration regulators of the present invention can control the concentration of serum remnant-like lipoproteins to the appropriate range and inhibit the increase of the postprandial concentration thereof, preferably in human whose BMI level is 23 or higher.

The forms of the serum remnant-like lipoprotein concentration regulators of the present invention are not particularly limited and may be those such as capsules and tablets. They may be added to food products, processed foods, beverages, seasonings, confectionery and pharmaceutical compositions and can be added to, for example, gelatin capsules, cooking fats and oils, dressing, butter, margarine, prepared margarine, fat spread, cream, ice cream, mayonnaise, shortening, bakery mix, breads, pies, cakes, cookies, doughnuts, muffins, scones, fry products, snacks, chocolates, toppings, processed meat products, frozen foods, fry products, enteral nutrients, intravenous nutrients and liquid diets.

Next, Examples will further illustrate the present invention. The following Examples only explain the present invention and do not particularly limit the invention.

EXAMPLE 1

Triglyceride of medium-chain fatty acids produced by The Nisshin OilliO Group, Ltd. (trade name: O.D.O) was used as Serum Remnant-like Lipoprotein Concentration Regulator 1. Meanwhile, 500 g of canola oil produced by The Nisshin OilliO Group, Ltd. was mixed with 500 g of triglyceride of medium-chain fatty acids produced by The Nisshin OilliO Group, Ltd. (trade name: O.D.O) to obtain 1 kg of Serum Remnant-like Lipoprotein Concentration Regulator 2. Further, 100 g of lard produced by Snow Brand Milk Products Co., Ltd. was mixed with 900 g of triglyceride of medium-chain fatty acids produced by The Nisshin OilliO Group, Ltd. (trade name: O.D.O) to obtain 1 kg of Serum Remnant-like Lipoprotein Concentration Regulator 3. 99.9% by weight of the fatty acids as components of the triglyceride of medium-chain fatty acids (trade name: O.D.O) were saturated fatty acids having 8 and 10 carbon atoms and weight ratio between the saturated fatty acids having 8 carbon atoms and those having 10 carbon atoms was 7.4:2.6. The proportion of the saturated fatty acids having 8 carbon atoms in the composition of fatty acids bonding to the second position of the triglyceride was 73% by weight. The proportion of the fatty acids bonding to the second position of the triglyceride was calculated by Brockerhoff method (Brockerhoff, H., "Stereospecific analysis of triglycerides: an alternative method", Journal of Lipid Research (U.S.A.), vol.8, No. 3, 167-169, 1967).

EXAMPLE 2

1 g of tocopherol produced by The Nisshin OilliO Group, Ltd. (trade name: Tocopherol 85) was added to 999 g of triglyceride of medium-chain fatty acids produced by The Nisshin OilliO Group, Ltd. (trade name: O.D.O), sufficiently stirred and dissolved to obtain 1 kg of Serum Remnant-like Lipoprotein Concentration Regulator 4. 99.9% by weight of the fatty acids as components of the triglyceride of medium-chain fatty acids were saturated fatty acids having 8 and 10 carbon atoms and weight ratio between the saturated fatty acids having 8 carbon atoms and those having 10 carbon atoms was 7.4:2.6. The proportion of the saturated fatty acids having 8 carbon atoms in the composition of fatty acids bonding to the second position of the triglyceride was 73% by weight.

EXAMPLE 3

20 g of plant sterol derived from rice oil was added to 980 g of the Serum Remnant-like Lipoprotein Concentration Regulator, sufficiently stirred and mixed to obtain Serum Remnant-like Lipoprotein Concentration Regulator 5.

EXAMPLE 4

Pilaf (Food Product 1 for controlling the concentration of serum remnant-like lipoproteins) was prepared by the following manner, using Serum Remnant-like Lipoprotein Concentration Regulator 1 of Example 1 as a cooking fat and oil. Food Product 1 for controlling the concentration of serum remnant-like lipoproteins contains 9.5 g of the Serum Remnant-like Lipoprotein Concentration Regulator 1 per serving.

Dispensation Ratio (Part by Weight)

320 parts of rice, 80 parts of onion, 80 parts of carrot, 94 parts of tomato ketchup, 5.3 parts of solid consomme (clear soup), 400 parts of water, and 48 parts of Serum Remnant-like Lipoprotein Concentration Regulator 1.

Production Method

Preparation method: Onion and carrot were chopped and fried with rice by Serum Remnant-like Lipoprotein Concentration Regulator 1. Then, the mixture was put into a rice kettle. Tomato ketchup, solid consommé (clear soup) and water were added thereto and cooked. The obtained food was divided into 260 g per serving.

The examination of the effect for controlling the postprandial concentration of serum remnant-like lipoproteins was carried out by the cross-over method, using Food Product 1 for controlling the concentration of serum remnant-like lipoproteins of Example 4. The pilaf prepared by the same amount of all-purpose salad oil (blend oil having its weight ratio as canola oil:soybean oil=70:30) was used as a control food. The examination was carried out with 29 healthy male adults. After fasting for 12 hours from a day before the examination day, Food Product 1 for controlling the concentration of serum remnant-like lipoproteins or the control food was ingested with commercially-available consomme soup (clear soup) to them in the morning of the examination. The fat and oil content per serving taking into account of the consomme soup of each of the example and the comparative example was 10.4 g. The collections of blood over time were carried out before eating and 2, 3, 4, 6, and 8 hours after eating, and serum RLP-cholesterol levels were determined by immunosorbent assay. Results thereof were evaluated by areas under the time-concentration curve calculated based on a quantitative value of each determination time with a trapezoidal method. The examination results thereof are indicated in Tables 1 and 2, and FIGS. 1, 2, 3 and 4. Meanwhile, the area under the time-concentration curve is a disposition function of an ingestion substance and represents the amount of absorption of the administered substance in the body per unit time. It is usually calculated with a trapezoidal method or an exponential method.

TABLE 1

Examination result of Food Product 1 for controlling the concentration of serum remnant-like lipoproteins (change values from 0 hour after eating; set initial value at 0 and calculated; numerical value is average value ± standard error)

|  | Time after eating | Control food | Food of the present invention |
|---|---|---|---|
| Serum RLP-cholesterol (mg/dl) | 0 hour | 0.00 ± 0.00 | 0.00 ± 0.00 |
|  | 2 hours | 1.91 ± 0.28 | 0.11 ± 0.17* |
|  | 3 hours | 1.57 ± 0.38 | −0.04 ± 0.17* |
|  | 4 hours | 0.31 ± 0.28 | −0.44 ± 0.21* |
|  | 6 hours | −0.79 ± 0.22 | −1.16 ± 0.19 |
|  | 8 hours | −0.85 ± 0.28 | −0.96 ± 0.22 |

*there is a significant difference compared with the control food (risk rate: less than 5%)

TABLE 2

Examination result of Food Product 1 for controlling the concentration of serum remnant-like lipoproteins (change values from 0 hour after eating; set initial value at 0 and calculated; numerical value is average value ± standard error)

|  | Time after eating | Control food | | Food of the present invention | |
|---|---|---|---|---|---|
|  |  | BMI23 or more | Less than BMI23 | BMI23 or more | Less than BMI23 |
| Serum RLP-cholesterol (mg/dl) | 0 hour | 0.00 ± 0.00 | 0.00 ± 0.00 | 0.00 ± 0.00 | 0.00 ± 0.00 |
|  | 2 hours | 2.11 ± 0.31 | 0.94 ± 0.55 | 0.30 ± 0.18* | −0.80 ± 0.08* |
|  | 3 hours | 1.82 ± 0.44 | 0.38 ± 0.40 | 0.04 ± 0.20* | −0.42 ± 0.18* |
|  | 4 hours | 0.57 ± 0.31 | −0.92 ± 0.22 | −0.40 ± 0.24* | −0.66 ± 0.29 |
|  | 6 hours | −0.68 ± 0.25 | −1.28 ± 0.33 | −1.09 ± 0.22 | −1.48 ± 0.11 |
|  | 8 hours | −0.78 ± 0.34 | −1.18 ± 0.32 | −0.94 ± 0.27 | −1.04 ± 0.19 |

*there is a significant difference compared with the control food (risk rate: less than 5%)

EXAMPLE 5

Fat spread (Food Product 2 for controlling the concentration of serum remnant-like lipoproteins) was prepared using Serum Remnant-like Lipoprotein Concentration Regulator 1 of Example 1. Food Product 2 for controlling the concentration of serum remnant-like lipoproteins contains 5 g of Serum Remnant-like Lipoprotein Concentration Regulator 1 per serving.

Dispensation Ratio (Part by Weight)

30.8 parts of purified processed fat and oil for cooking, 10 ppm of 30%,β-carotene, 0.5 parts of an emulsifying agent, 27.2 parts of water, 1.1 parts of salt, 1 part of powdered milk, 0.1 parts of a flavoring agent, and 39.3 parts of Serum Remnant-like Lipoprotein Concentration Regulator 1.

Production Method

Preparation method: Serum Remnant-like Lipoprotein Concentration Regulator 1 is mixed under heating with purified processed fat and oil for cooking, 30% β-carotene, an emulsifying agent and a flavoring agent. Then, after water, salt and powdered milk are added thereto and preliminarily emulsified, the mixture is kneaded under quenching.

The examination of the effect for controlling the postprandial concentration of serum remnant-like lipoproteins was carried out by the cross-over method, using Food Product 2 for controlling the concentration of serum remnant-like lipoproteins of Example 5. The fat spread prepared by the same amount of all-purpose salad oil (blend oil having its weight ratio as canola oil:soybean oil=70:30) was used as a control food. The examination was carried out with 31 healthy adults (15 males, 16 females). After fasting for 12 hours from a day before the examination day, Food Product 2 for controlling the concentration of serum remnant-like lipoproteins or the control food was ingested with commercially-available bread by them in the morning of the examination. The fat and oil content per serving taking into account of the bread of each of the example and the comparative example was 15.8 g. The collections of blood over time were carried out before eating and 2, 4 and 6 hours after eating, and serum RLP-cholesterol levels were determined by immunosorbent assay. Results thereof were evaluated by areas under the time-concentration curve calculated based on a quantitative value of each determination time with a trapezoidal method. The examination results thereof are indicated in Tables 3 and 4, and FIGS. 5, 6, 7 and 8. Meanwhile, the area under the time-concentration curve is a disposition function of an ingestion substance and represents the amount of absorption of the administered substance in the body per unit time. It is usually calculated with a trapezoidal method or an exponential method.

TABLE 3

Examination result of Food Product 2 for controlling the concentration of serum remnant-like lipoproteins (change values from 0 hour after eating; set initial value at 0 and calculated; numerical value is average value ± standard error)

|  | Time after eating | Control food | Food of the present invention |
|---|---|---|---|
| Serum RLP-cholesterol (mg/dl) | 0 hour | 0.00 ± 0.00 | 0.00 ± 0.00 |
|  | 2 hours | 3.38 ± 2.05 | 2.25 ± 1.48* |
|  | 4 hours | 2.28 ± 1.84 | 1.78 ± 1.58 |
|  | 6 hours | 1.51 ± 1.81 | 1.11 ± 1.17 |

*there is a significant difference compared with the control food (risk rate: less than 5%)

TABLE 4

Examination result of Food Product 2 for controlling the concentration of serum remnant-like lipoproteins (change values from 0 hour after eating; set initial value at 0 and calculated; numerical value is average value ± standard error)

| | | Control food | | Food of the present invention | |
|---|---|---|---|---|---|
| | Time after eating | BMI23 or more | Less than BMI23 | BMI23 or more | Less than BMI23 |
| Serum RLP-cholesterol (mg/dl) | 0 hour | 0.00 ± 0.00 | 0.00 ± 0.00 | 0.00 ± 0.00 | 0.00 ± 0.00 |
| | 2 hours | 3.66 ± 2.03 | 2.94 ± 2.11 | 2.58 ± 1.57* | 1.73 ± 1.21 |
| | 4 hours | 2.45 ± 1.48 | 2.01 ± 2.35 | 2.03 ± 1.59 | 1.38 ± 1.54 |
| | 6 hours | 1.62 ± 1.56 | 1.33 ± 2.21 | 1.21 ± 0.96 | 0.94 ± 1.49 |

*there is a significant difference compared with the control food (risk rate: less than 5%)

Figure 1:
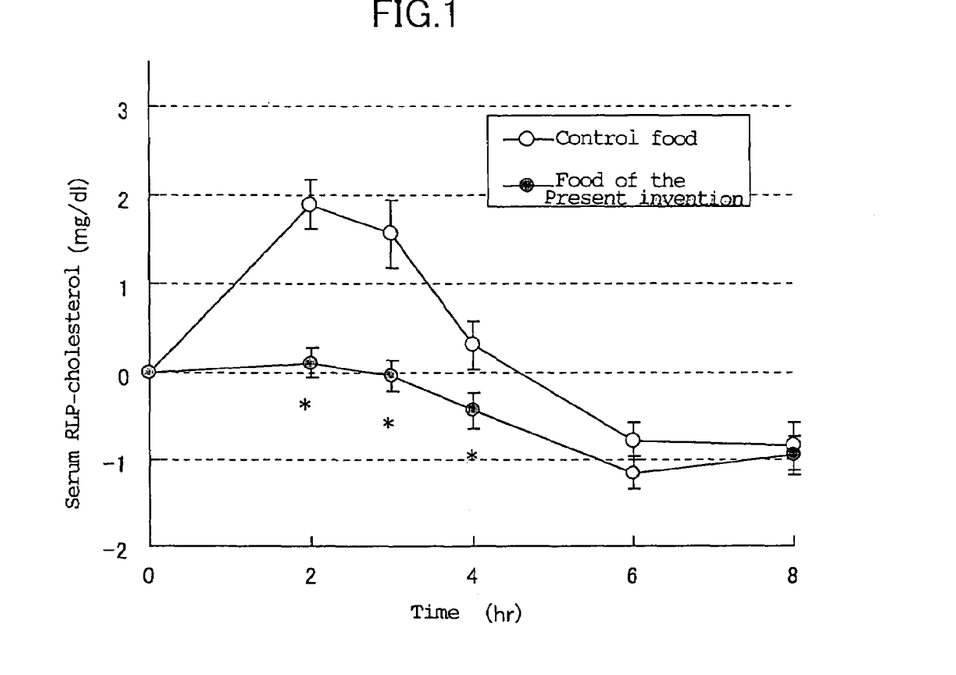
FIG. 1 is a graph showing changes over time (set initial value at 0 and calculated) in the concentration of serum RLP-cholesterol until 8 hours after eating Food Product 1 for controlling the concentration of serum remnant-like lipoproteins.
Figure 2:
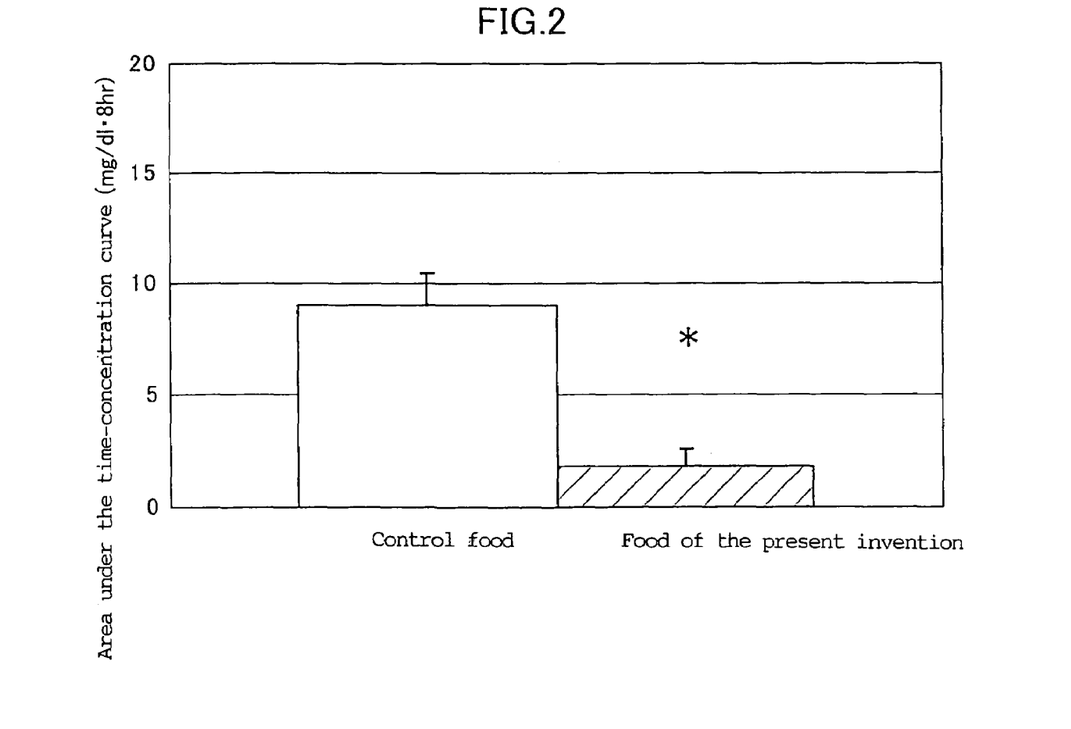
FIG. 2 is a graph showing areas under the time-concentration curve of serum RLP-cholesterol until 8 hours after eating Food Product 1 for controlling the concentration of serum remnant-like lipoproteins.

As indicated in Table 1 and FIG. 1, the increase of the postprandial concentration of the serum remnant-like lipoproteins was significantly inhibited as compared with the control food by ingesting Food Product 1 for controlling the concentration of serum remnant-like lipoproteins of the present invention, after eating, especially 2, 3 and 4 hours after eating. Similarly, as indicated in Table 3 and FIG. 5, the increase of the postprandial concentration of the serum remnant-like lipoproteins was significantly inhibited as compared with the control food by ingesting the Food Product 2 for controlling the concentration of serum remnant-like lipoproteins of the present invention, 2 hours after eating. From these, it is clear that production of the serum remnant-like lipoproteins has been significantly decreased. Further, it is also clear from FIGS. 2 and 6 that Food Products 1 and 2 for controlling the concentration of serum remnant-like lipoproteins indicated significantly lower values as compared with the control foods in the amounts of the remnant-like lipoproteins which developed in the blood by 8 or 6 hours after eating, and, therefore, production of the serum remnant-like lipoproteins has been decreased. From these, it is clarified that Food Products 1 and 2 for controlling the concentration of serum remnant-like lipoproteins which contain the serum remnant-like lipoprotein concentration regulators of the present invention inhibit the increase of the postprandial concentration of the serum remnant-like lipoproteins.

Figure 3:
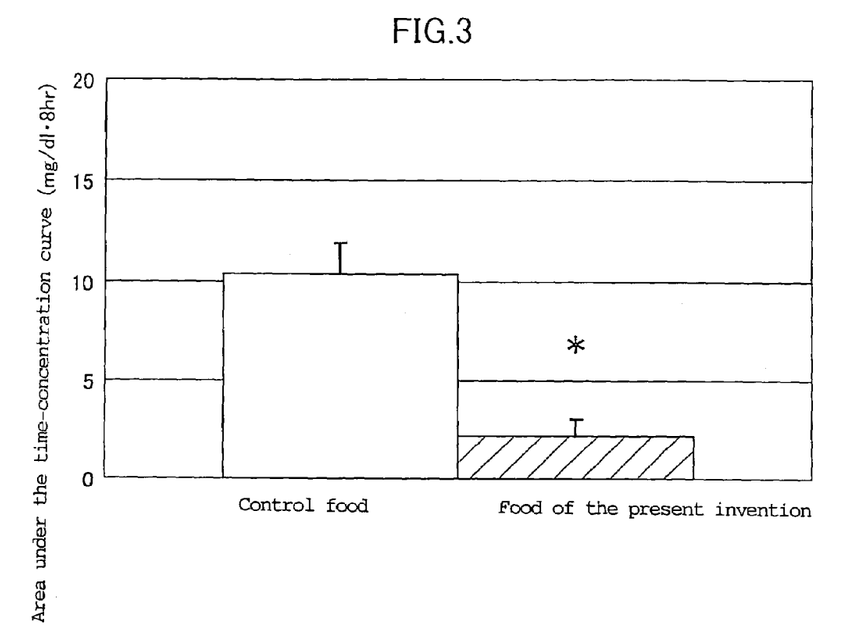
FIG. 3 is a graph showing areas under the time-concentration curve (of a group consisting of those whose BMI level is 23 or higher) of the amount of serum RLP-cholesterol until 8 hours after eating Food Product 1 for controlling the concentration of serum remnant-like lipoproteins.
Figure 4:
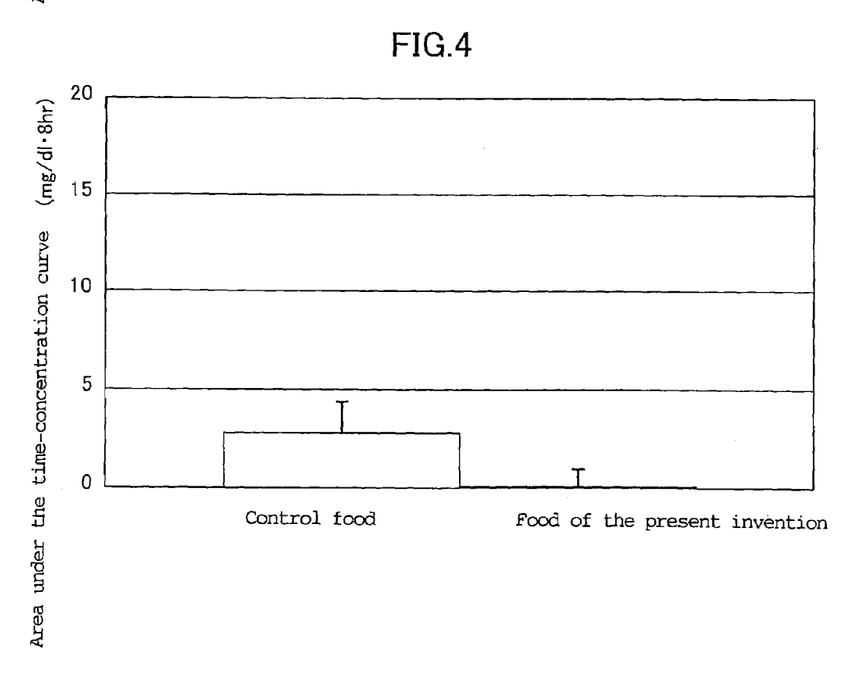
FIG. 4 is a graph showing areas under the time-concentration curve (of a group consisting of those whose BMI level is lower than 23) of the amount of serum RLP-cholesterol until 8 hours after eating Food Product 1 for controlling the concentration of serum remnant-like lipoproteins.
Figure 5:
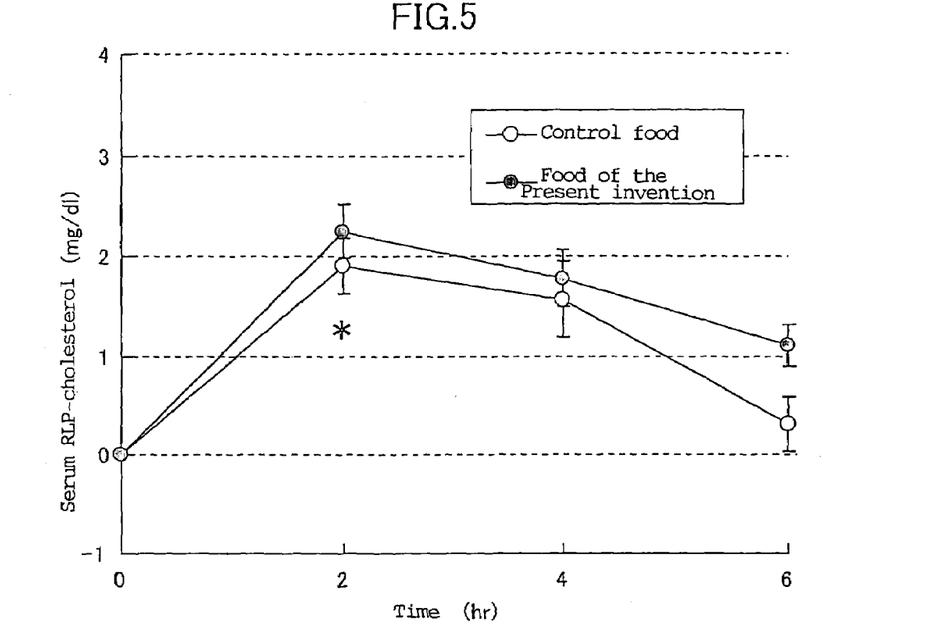
FIG. 5 is a graph showing changes over time (set default value at 0 and calculated) in the concentration of serum RLP-cholesterol until 6 hours after eating Food Product 2 for controlling the concentration of serum remnant-like lipoproteins.
Figure 6:
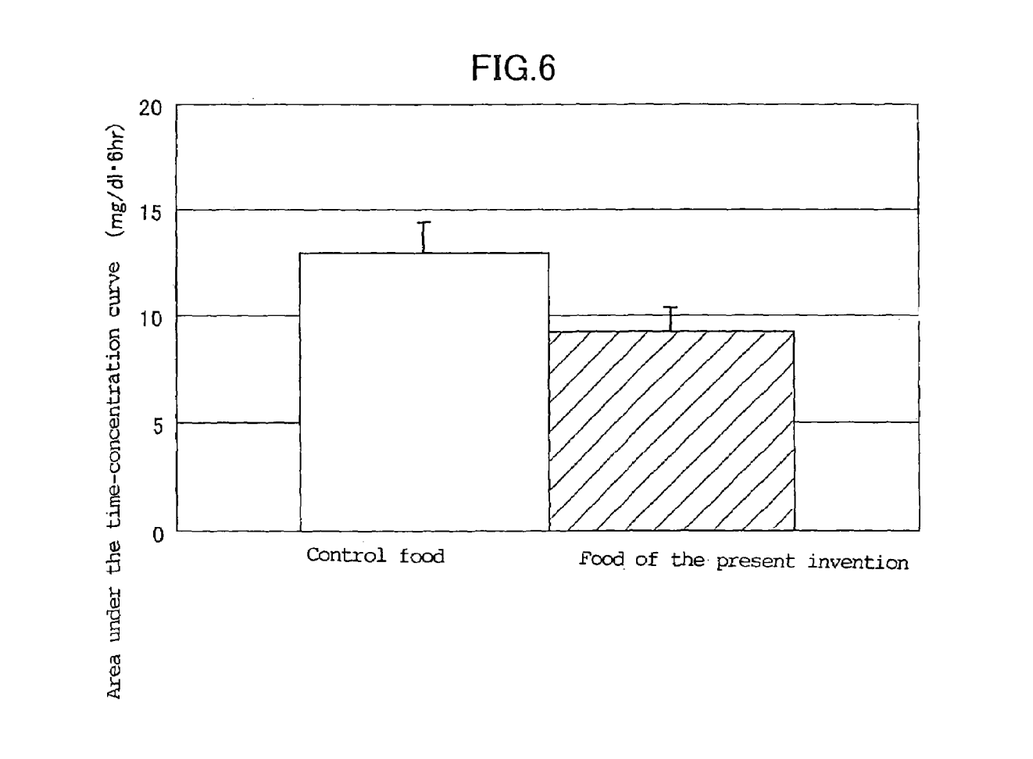
FIG. 6 is a graph showing areas under the time-concentration curve of the amount of serum RLP-cholesterol until 6 hours after eating Food Product 2 for controlling the concentration of serum remnant-like lipoproteins.
Figure 7:
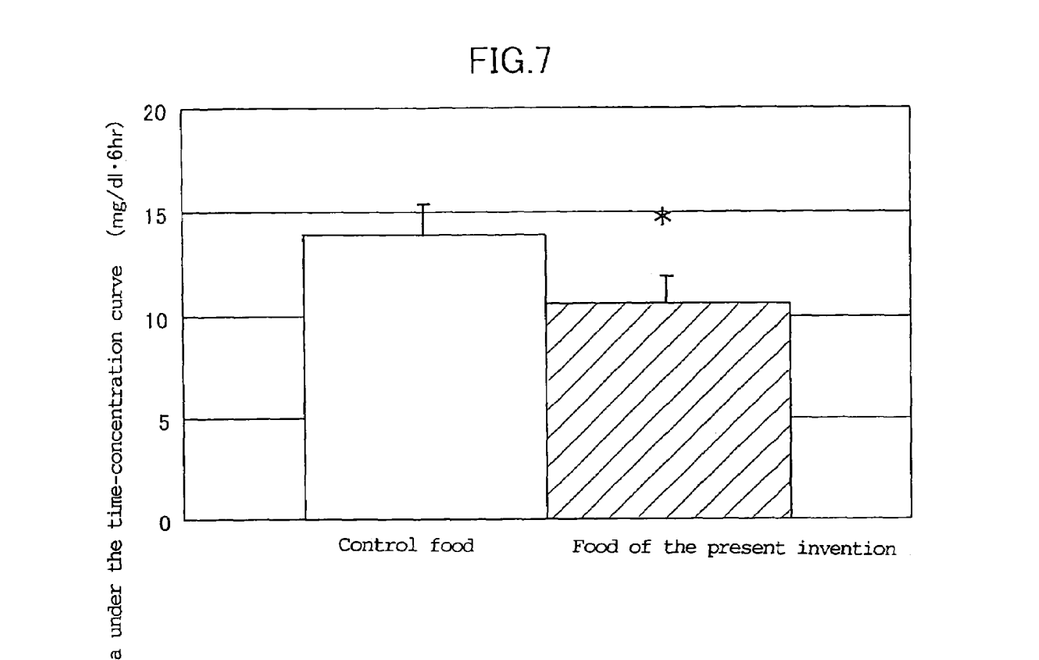
FIG. 7 is a graph showing areas under the time-concentration curve (of a group consisting of those whose BMI level is 23 or higher) of the amount of serum RLP-cholesterol until 6 hours after eating Food Product 2 for controlling the concentration of serum remnant-like lipoproteins.
Figure 8:
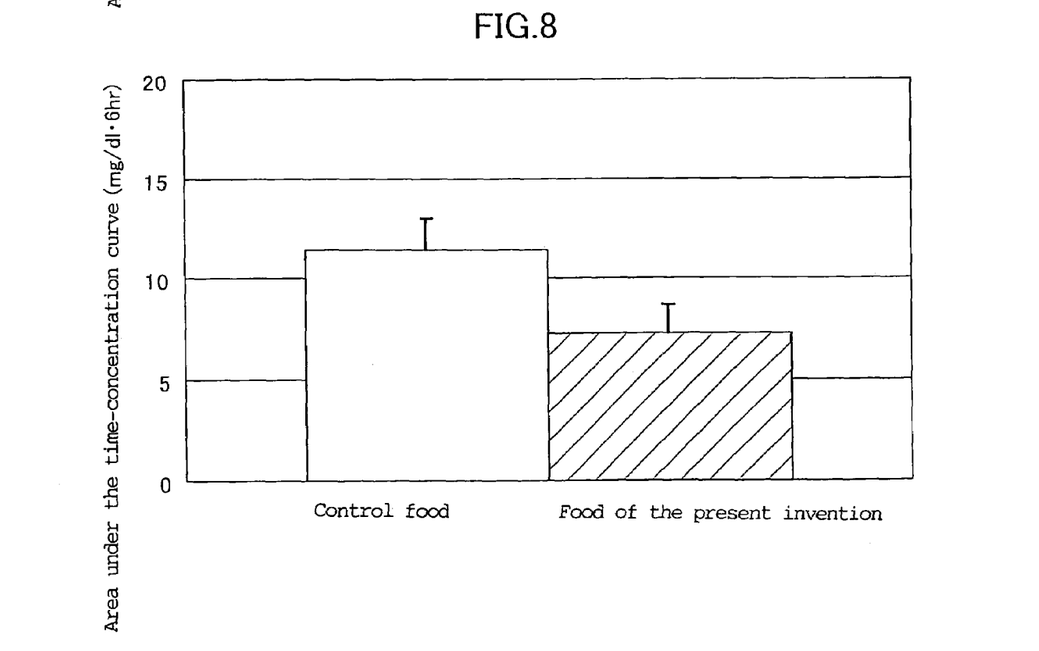
FIG. 8 is a graph showing areas under the time-concentration curve (of a group consisting of those whose BMI level is lower than 23) of the amount of serum RLP-cholesterol until 6 hours after eating Food Product 2 for controlling the concentration of serum remnant-like lipoproteins.

Further, as indicated in Table 2, FIGS. 3 and 4, Table 4 and FIGS. 7 and 8, when a group of human whose BMI levels are 23 or higher and that of human whose BMI levels are lower than 23 are compared in case of ingesting Food Products 1 and 2 for controlling the concentration of serum remnant-like lipoproteins which contain the serum remnant-like lipoprotein concentration regulators of the present invention, it is clarified that Food Products 1 and 2 for controlling the concentration of serum remnant-like lipoproteins inhibit the increase of the postprandial concentration of the serum remnant-like lipoproteins, especially in human whose BMI levels are 23 or higher.

Meanwhile, reference marks "*" shown in FIGS. 1, 2, 3, 5, 6 and 7 indicate that, when Food Products 1 and 2 for controlling the concentration of serum remnant-like lipoproteins which contain the serum remnant-like lipoprotein concentration regulators of the present invention are ingested, average values thereof indicate statistically significant difference (risk rate: less than 5%) compared with those of the control foods.

The present invention can provide highly effective, safe, and easily carried out serum remnant-like lipoprotein concentration regulators and foods containing the serum remnant-like lipoprotein concentration regulators, and pharmaceutical compositions containing the serum remnant-like lipoprotein concentration regulators. Since the concentration of serum remnant-like lipoproteins can be controlled to the appropriate range by routinely ingesting the serum remnant-like lipoprotein concentration regulators of the present invention, it makes possible to prevent the lifestyle-related diseases such as hyperlipidemia and can expect a preventive effect of vascular diseases derived from intake of excess lipids such as arterial sclerosis. The effect is more effective particularly in human whose BMI level is higher (preferably BMI level is 23 or higher).

What is claimed is:

1. A method of controlling the concentration of the serum remnant-like lipoprotein in a subject, which comprises administering an effective amount of a serum remnant-like lipoprotein concentration regulator comprising medium-chain triglyceride to the subject, wherein:

the subject is a human, the subject's BMI level is 23 or higher, and 95 to 100% by weight of the fatty acids that are components of the medium-chain triglyceride are saturated fatty acids having 8 or 10 carbon atoms; the weight ratio between the saturated fatty acids having 8 carbon atoms and those having 10 carbon atoms is 7/3 to 8/2; and the proportion of the saturated fatty acids having 8 carbon atoms in all the fatty acids bonding to the second position of the triglyceride is 65 to 80% by weight.

2. The method according to claim 1, wherein the medium-chain triglyceride is a triester of saturated fatty acids having 6 to 12 carbon atoms and glycerin.

3. The method according to claim 1, wherein the medium-chain triglyceride is a triester of caprylic acid, capric acid, and glycerin.

4. The method according to claim 1, wherein the serum remnant-like lipoprotein concentration regulator comprises 5% or more by weight of the medium-chain triglyceride.

5. The method according to claim 4, wherein the serum remnant-like lipoprotein concentration regulator comprises 40% or more by weight of the medium-chain tryglyceride.

6. The method according to claim 5, wherein the serum remnant-like lipoprotein concentration regulator comprises 40 to 99.95% by weight of the medium-chain triglyceride.

7. The method according to claim 1, wherein the serum remnant-like lipoprotein concentration regulator further comprises animal and plant fats and oils.

8. The method according to claim 1, wherein the serum remnant-like lipoprotein concentration regulator further comprises vitamin E.

9. The method according to claim 1, wherein the serum remnant-like lipoprotein concentration regulator further comprises plant sterol.

* * * * *